(12) United States Patent
Rueda et al.

(10) Patent No.: US 10,858,690 B2
(45) Date of Patent: Dec. 8, 2020

(54) PROCESSING BLOOD SAMPLES TO DETECT TARGET NUCLEIC ACIDS

(71) Applicant: MONOLYTHIX, INC., Camarillo, CA (US)

(72) Inventors: Ivan Rueda, Pacoima, CA (US); Ian McFadden, Oxnard, CA (US); Mark D. Dobbs, Brea, CA (US); Victor Shum, Thousand Oaks, CA (US); Keith A. Oberg, Newhall, CA (US); Anthony Spence, Newbury Park, CA (US); Walt Caldwell, Thousand Oaks, CA (US)

(73) Assignee: Monolythix, Inc., Camarillo, CA (US)

( * ) Notice: Subject to any disclaimer, the term of this patent is extended or adjusted under 35 U.S.C. 154(b) by 258 days.

(21) Appl. No.: 15/605,099

(22) Filed: May 25, 2017

(65) Prior Publication Data

US 2017/0342464 A1 Nov. 30, 2017

Related U.S. Application Data

(60) Provisional application No. 62/341,559, filed on May 25, 2016.

(51) Int. Cl.

| | | |
|---|---|---|
| C12Q 1/6806 | (2018.01) | |
| C08F 222/10 | (2006.01) | |
| B01L 3/00 | (2006.01) | |
| C08J 9/00 | (2006.01) | |
| C08J 9/12 | (2006.01) | |
| C08J 9/14 | (2006.01) | |
| G01N 33/49 | (2006.01) | |
| B29C 35/08 | (2006.01) | |
| B29C 67/20 | (2006.01) | |
| G01N 1/40 | (2006.01) | |
| C08F 2/38 | (2006.01) | |
| B29K 105/00 | (2006.01) | |
| B29K 105/04 | (2006.01) | |

(52) U.S. Cl.
CPC .......... *C12Q 1/6806* (2013.01); *B01L 3/5023* (2013.01); *B29C 35/0805* (2013.01); *B29C 67/202* (2013.01); *C08F 222/1006* (2013.01); *C08J 9/0023* (2013.01); *C08J 9/0033* (2013.01); *C08J 9/125* (2013.01); *C08J 9/142* (2013.01); *G01N 1/405* (2013.01); *G01N 33/491* (2013.01); *B01L 2200/0647* (2013.01); *B01L 2200/12* (2013.01); *B01L 2300/069* (2013.01); *B01L 2300/0825* (2013.01); *B01L 2300/0887* (2013.01); *B01L 2300/12* (2013.01); *B01L 2400/0406* (2013.01); *B29C 2035/0827* (2013.01); *B29K 2105/0002* (2013.01); *B29K 2105/04* (2013.01); *C08F 2/38* (2013.01); *C08J 2335/02* (2013.01)

(58) Field of Classification Search
None
See application file for complete search history.

(56) References Cited

U.S. PATENT DOCUMENTS

| | | | |
|---|---|---|---|
| 6,693,159 B1 | 2/2004 | Holmes et al. | |
| 9,464,969 B2 | 10/2016 | Oberg et al. | |
| 9,606,032 B2 | 3/2017 | Gooley et al. | |
| 2005/0095602 A1 | 5/2005 | West et al. | |
| 2012/0024788 A1 | 2/2012 | Kelso et al. | |
| 2012/0230887 A1 | 9/2012 | Zucchelli | |
| 2012/0276576 A1* | 11/2012 | Haddad | C08F 265/04 435/29 |
| 2015/0321191 A1 | 11/2015 | Kendall et al. | |
| 2016/0146714 A1 | 5/2016 | Oberg et al. | |
| 2016/0290902 A1 | 10/2016 | Gooley et al. | |
| 2017/0342466 A1 | 11/2017 | Rueda et al. | |

FOREIGN PATENT DOCUMENTS

| | | |
|---|---|---|
| WO | 2005/098439 A2 | 10/2005 |
| WO | 2011082449 A1 | 7/2011 |
| WO | 2013006904 A1 | 1/2013 |

OTHER PUBLICATIONS

Zhong et al. In situ polymerization of monolith based on poly(Triallyl Isocyanurate-co-trimethylolpropane triacrylate) and its application in high-performance liquid chromatography. J Chromatogr Sci. 53(4):531-6 (2014).

Viklund et al. Molded macroporous poly(glycidyl methacrylate-co-trimethylolpropane trimethacrylate) materials with fine controlled porous properties: preparation of monoliths using photoinitiated polymerization. Chem Mater. 9(2): 463-71 (1997).

\* cited by examiner

*Primary Examiner* — Robert T Butcher
(74) *Attorney, Agent, or Firm* — McCarter & English, LLP; Basil S. Krikelis; Michael J. DeGrazia

(57) ABSTRACT

Provided herein are porous polymer monolith materials and processes that enable integration of blood fractionation, specific nucleic acid amplification and/or detection of nucleic acids from whole blood.

15 Claims, 12 Drawing Sheets

PROCESSING BLOOD SAMPLES TO DETECT TARGET NUCLEIC ACIDS

CROSS REFERENCE TO RELATED APPLICATIONS

This application claims priority to U.S. Provisional Application Ser. No. 62/341,559 filed on May 25, 2016, the contents of which are incorporated herein by reference.

FIELD OF THE TECHNOLOGY

The present disclosure is related to lateral flow porous polymer monoliths for processing blood samples and detecting the presence of target nucleic acids as well as the methods of making and using such monoliths.

BACKGROUND

Testing of blood samples to detect target nucleic acids can be challenging. The sensitivity and specificity of nucleic acid-based blood assays are influenced not only by the abundance of the nucleic acid, but by its availability for amplification and detection. For example, the availability may be affected if the nucleic acid is sequestered in viral capsids or if it is associated with bound proteins. More importantly, the components of blood cells have well-known interfering effects on nucleic acid diagnostic techniques, such as inhibition of amplification and signal detection. A number of solutions have been developed to deal with this problem.

Most nucleic acid detection systems require a pre-extraction of total nucleic acids in samples before application to the amplification and detection system. Some nucleic acid extraction protocols involve lysing all blood cells, binding nucleic acids, and successfully washing away inhibitory substances. Alternatively, whole blood can be centrifuged to remove red and white blood cells from plasma, separating the cells from plasma-borne nucleic acids and pathogens. Plasma separation performed in this manner works well but is not ideal for large numbers of samples and increases contamination risks due to additional blood handling steps. Simpler methods for pre-processing lysed blood samples for direct nucleic acid analysis have been developed. Generally, small amounts of blood are lysed in reagents that sequester inhibitory substances. These specially-treated blood samples are then used in small amounts in amplification reactions containing specialized buffers and inhibition-tolerant enzymes. However, the enzymes required for these techniques are more expensive than standard amplification enzymes. Furthermore, there are stricter limitations on the amount of sample and the methods that can be used to analyze these preparations, possibly reducing assay sensitivity.

Given these disadvantages, and the increasing demand for inexpensive consumable detection methods particularly in remote diagnostic medicine or at sites with minimally-skilled technical personnel, the need exists for simple Point-of-Care (POC) tools for the detection of nucleic acids in blood. Such ideal detection devices for blood should be able to receive whole blood or minimally diluted whole blood; eliminate or segregate inhibitory substances away from the amplification and detection reagents; and operate quickly, inexpensively, and in a fully integrated system with minimal requirements for user or instrument intervention.

SUMMARY

Provided herein are porous polymer monolith materials and processes that enable integration of blood fractionation, specific nucleic acid amplification and/or detection of nucleic acids from whole blood. The disclosed porous polymer monoliths are self-wicking and are amenable to methods that provide simple target nucleic acid isolation, amplification, and/or detection methods from blood that minimizes or eliminates the need for hazardous chemicals or specialized equipment.

In one aspect, the disclosed porous polymer monoliths are universal nucleic acid detection systems: small homogeneous strips capable of rapidly separating blood into red-cell-containing and red-cell-free components, absorbing wet amplification and detection reagents designed to detect a single target molecule of interest, and supporting a detection reaction within the monolith. See e.g., FIG. 6. The disclosed polymer monoliths and related devices not only allow for multiple target detection within a single sample (e.g., using target specific multiplex amplification, and multi-modal detection (e.g. multiple fluorescent dyes) within a single reagent zone), but they can be further utilized by geometrically distributing samples through radial wicking in monolith discs or dendritic processes emanating from the sample loading zone. See e.g., FIGS. 7-10.

The disclosed monoliths are designed to be physically robust while retaining their critical diagnostic advantages. As such, they can stand alone, be molded into a wide variety of shapes, and be integrated into existing hardware/consumable systems.

DETAILED DESCRIPTION

Figure 1:
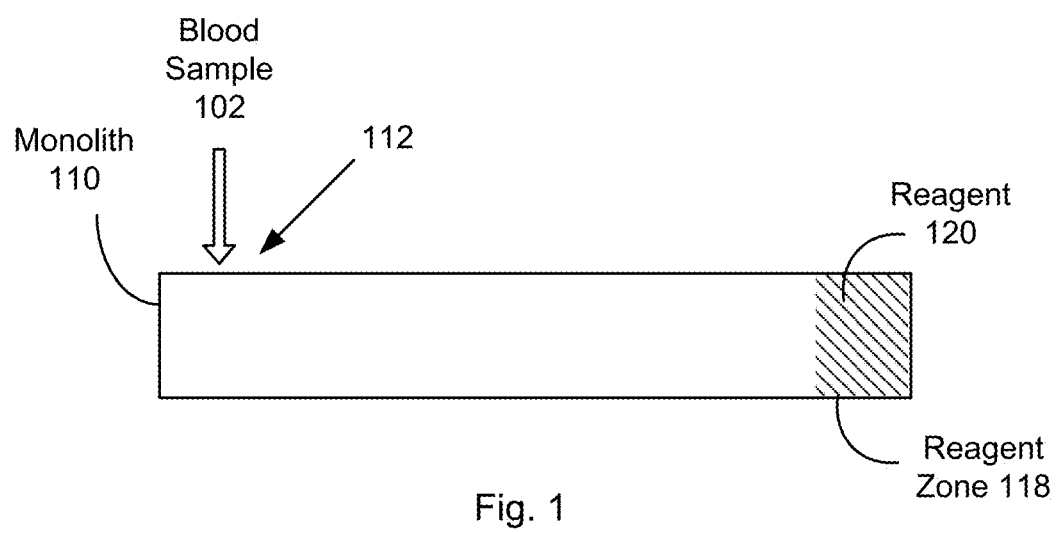
FIG. 1 shows a view of a monolith for processing a blood sample.

Provided herein are porous polymer monoliths that enable integration of blood fractionation, specific nucleic acid amplification, detection of nucleic acids from whole blood, and self-wicking devices. The disclosed polymer monoliths can be fabricated by e.g., i) providing a plurality of monomers comprising: at least one monomer; and at least one radically polymerizable trimethylolpropane (TMP)-based monomer having the formula:

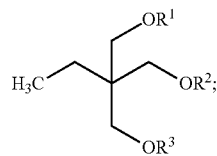

wherein $R^1$, $R^2$, and $R^3$ are each independently selected from —$(CH_2CH_2O)_nH$, —$(CH_2CH_2O)_nC(O)CH_2CH_2SH$, —$(CH_2CH_2O)_nC(O)CH=CH_2$, and —$(CH_2CH_2O)_nC(O)C(CH_3)=CH_2$; and each n is independently an integer from 0 to 12, wherein said (TMP)-based monomer is present in an amount ranging from 0.1% to 44% (v:v) of the total volume of the plurality of monomers; ii) obtaining a polymerizable composition by combining the plurality of monomers in a porogenic solvent; and iii) polymerizing the polymerizable composition to form the porous polymer monolith.

In one aspect, n in the (TMP)-based monomer described herein each n is independently an integer from 0 to 6, an integer from 0 to 3, or the integer 0, 1, 2, or 3. In one aspect, each n is 0.

In one aspect, monoliths of the present methods are self-wicking.

The term "self-wicking" refers to the movement of fluid through a monolith due to the effect of capillary action by the monolith pores on a liquid. This is the property of the monoliths that causes a liquid sample to flow spontaneously from a first portion of a monolith to another continuous portion without the need for an external pressure differential to be applied (pressure is used, for example, in conventional column chromatography). This self-wicking ability may alone provide the forces necessary to transport and process a blood sample during the methods described herein. Self-wicking is independent of the orientation of the monolith in space and sufficient to overcome the force of gravity on wicked fluids, resulting in a generally anisotropic flow of wicked fluid within the monolith. As such, the flow of liquids within self-wicking monoliths is generally directed by the geometry of the monolith. Advantageously, this property may be utilized by wicking fluids through monoliths of defined geometry and aspect ratio so as to predictably direct the flow of fluids. For example, a lateral flow device may be developed by applying fluid to a monolith that is suitably long and thin relative to its width. The monoliths described herein are suitably self-wicking. For example, in certain aspects, monoliths of the present methods comprise a two-minute water wick rate between 1.0 and 10 centimeters such as e.g., between 1.5 and 5.0 centimeters. In other instances, monoliths of the present methods comprise a two-minute water wick rate of at least 1.8 cm, at least 2.0 cm, at least 2.3 cm, at least 2.5 cm, at least 2.7 cm, at least 3.0 cm, at least 3.2 cm, at least 3.5 cm, at least 4.0 cm, at least 4.5 cm, at least 5.0 cm, at least 5.5 cm, at least 6.0 cm, at least 6.5 cm, at least 7.0 cm, or at least 7.5 cm.

In addition to the self-wicking properties, monoliths of the present methods are suitable for fractionating biological fluid such as blood. In one aspect, monoliths of the present methods fractionate red blood cells. Red blood cell (RBC) retention factor (Rf) is a measure analogous to the retardation factor used in planar or thin layer chromatography. For a monolith of constant cross-sectional area, the RBC Rf is calculated as the ratio of the distance traversed by the farthest observable RBCs (generally a linear front) to the analogous total distance traversed by the blood-cell-free fluid, starting from the proximal edge of the blood loading location. This is visually represented as a blood-red zone and an adjacent zone that is faintly nude or yellow in color. The RBC Rf is used to measure the relative ability of monoliths to fractionate blood by retarding the movement of blood cells relative to the other constituents of blood. Here, in one aspect, the monoliths of the present methods have a measured red blood cell retention factor (Rf) value in the range of 0.01 to 0.8. In other aspects, monoliths of the present methods have a measured red blood cell retention factor (Rf) value in the range of 0.01 to 0.8 and comprise a two-minute water wick rate between 1.5 and 5.0 centimeters.

The pore size of monoliths of the present methods can vary. In one aspect, the pore size of monoliths of the present methods is within a range of 2-7 microns. In other aspects, monoliths of the present methods have a measured red blood cell retention factor (Rf) value in the range of 0.01 to 0.8 and a pore size within a range of 2-7 microns. In another aspect, monoliths of the present methods have a measured red blood cell retention factor (Rf) value in the range of 0.01 to 0.8, comprise a two-minute water wick rate between 1.5 and 5.0 centimeters, and have a pore size within a range of 2-7 microns.

The porosity of monoliths of the present methods can also vary. In certain instances, the porosity of monoliths of the present methods is 50 to 85 percent. In other aspects, monoliths of the present methods have a measured red blood cell retention factor (Rf) value in the range of 0.01 to 0.8 and a porosity of 50 to 85 percent. In another aspect, monoliths of the present methods have a measured red blood cell retention factor (Rf) value in the range of 0.01 to 0.8, comprise a two-minute water wick rate between 1.5 and 5.0 centimeters, and have a porosity of 50 to 85 percent. In yet another aspect, monoliths of the present methods have a measured red blood cell retention factor (Rf) value in the range of 0.01 to 0.8, comprise a two-minute water wick rate between 1.5 and 5.0 centimeters, have a pore size within a range of 2-7 microns, and have a porosity of 50 to 85 percent.

Monoliths of the present methods can comprise a minimum tensile strength corresponding to a supported weight of at least 10 grams. This can be determined e.g., by the test protocol described in FIG. 14. Thus, in one aspect, provided are monoliths having a measured red blood cell retention factor (Rf) value in the range of 0.01 to 0.8 and a minimum weight support of 10 grams. Also provided are monoliths having a measured red blood cell retention factor (Rf) value in the range of 0.01 to 0.8, a porosity of 50 to 85 percent, and a minimum weight support of 10 grams. Also provided are monoliths having a measured red blood cell retention factor (Rf) value in the range of 0.01 to 0.8, a two-minute water wick rate between 1.5 and 5.0 centimeters, a porosity of 50 to 85 percent, and a minimum weight support of 10 grams. Further provided are monoliths having a measured red blood cell retention factor (Rf) value in the range of 0.01 to 0.8, a two-minute water wick rate between 1.5 and 5.0 centimeters, a porosity of 50 to 85 percent, a porosity of 50 to 85 percent, and a minimum weight support of 10 grams. In other aspects, monoliths of the present methods can comprise a minimum weight support corresponding to a supported weight of at least 50 grams, at least 100 grams, at least 250 grams, at least 500 grams, at least 750 grams, at least 1000 grams, at least 1250 grams, at least 1500 grams or higher.

In certain instances, the at least one TMP-based monomer of the disclosed methods comprises trimethylolpropane ethoxy triacrylate (TMP(EO)TA). The TMP(EO)TA may be present in an amount ranging from 0.1% to 44% (v:v) based on the total volume of the plurality of monomers.

In certain instances, the at least one TMP-based monomer of the disclosed methods comprises trimethylolpropane tris (3-mercaptopropionate) (TMPMP). The TMPMP may be present in an amount ranging from 0.1% to 7% (v:v) based on the total volume of the plurality of monomers.

In certain instances, the at least one monomer of the disclosed methods is selected from ethylene glycol dimethacrylate (EGDMA); 2-hydroxyethyl methacrylate (HEMA); tetra(ethylene glycol) diacrylate (TEGDA); tetra(ethylene glycol) dimethacrylate (TEGDMA); and a combination thereof including two or more of the EGDMA, HEMA, TEGDA or TEGDMA.

In certain instances, the at least one monomer of the disclosed methods is selected from ethylene glycol dimethacrylate (EGDMA) in an amount ranging from 34% to 75% (v:v) of the total volume of the plurality of monomers; 2-hydroxyethyl methacrylate (HEMA) in an amount ranging from 10% to 35% (v:v) of the total volume of the plurality of monomers; tetra(ethylene glycol) diacrylate (TEGDA) in an amount ranging from 0% to 15% (v:v) of the total volume of the plurality of monomers; and tetra(ethylene glycol) dimethacrylate (TEGDMA) in an amount ranging from 0% to 20% (v:v) of the total volume of the plurality of monomers.

The porogenic solvent of the methods described herein may be alcoholic, i.e., comprises at least one alcohol. In one aspect, the porogenic solvent comprises a mixture of alcohol and water. In another aspect, the porogenic solvent comprises a mixture of two alcohols. In another aspect, the porogenic solvent comprises a mixture of two alcohols and water. Water may be present in an amount ranging from 0% to 10%.

In one aspect, the porogenic solvent of the methods described herein comprises a first alcohol of the molecular formula: $[C_XH_{(2X+2)}O]$, wherein X is an integer from 1 to 10. In another aspect, the porogenic solvent of the methods described herein comprises a first alcohol of the molecular formula: $[C_XH_{(2X+2)}O]$, wherein the first alcohol is present in an amount ranging from 0 to 100% of the total volume of the porogenic solvent.

In one aspect, the porogenic solvent of the methods described herein comprises a second alcohol of the molecular formula: $[C_YH_{(2Y+2)}O_2]$, wherein Y is an integer from 2 to 10. In another aspect, the porogenic solvent of the methods described herein comprises a second alcohol of the molecular formula: $[C_YH_{(2Y+2)}O_2]$, wherein the second alcohol is present in an amount ranging from 0 to 50% of the total volume of the porogenic solvent. In one aspect, the alcohols may include the following mixture: methanol from 20% to 65% (v:v), octanol from 0% to 60% (v:v) and pentane diol from 0% to 35% (v:v).

In one aspect, the porogenic solvent of the methods described herein further comprises a surfactant. In another aspect, the porogenic solvent of the methods described herein further comprises a surfactant selected from sodium dodecyl sulfate (SDS), Poloxamer 124, and Triton X-100. In another aspect, the porogenic solvent of the methods described herein further comprises a surfactant selected from SDS present in an amount ranging from 0 to 1.0% of the total volume of the porogenic solvent, Poloxamer 124 present in an amount ranging from 0 to 35% of the total volume of the porogenic solvent, and Triton X-100 present in an amount ranging from 0 to 35% of the total volume of the porogenic solvent.

In one aspect, the polymerizable composition of the methods described herein has a monomer to solvent ratio of 1:1 to 1:5 (v:v).

As is well known to those skilled in the art, after polymerization of a monolith has been completed, the monolith is washed to remove the remaining solvent and any unincorporated monomers in the monolith and thoroughly dried to prepare the monolith for wicking. Various methods are known for the washing and drying of monoliths.

Also provided herein are porous polymer monoliths made by any one of the methods described herein and which have one or more of the disclosed properties, e.g., self-wicking (such as a two-minute water wick rate between 1.5 and 5.0 centimeters), an Rf value in the range of 0.01 to 0.8, a pore size within a range of 2-7 microns, a porosity of 50 to 85 percent, and a minimum weight support of 10 grams.

Also provided herein are methods for detecting a target nucleic acid in a blood-cell-free fraction of a blood sample, comprising: i) providing a monolith fabricated according to the methods described herein, wherein at least one zone of the monolith is designated as a reagent zone; ii) loading at least one amplification and/or detection reagent for a target nucleic acid into the reagent zone of the monolith; iii) optionally drying the at least one reagent in the monolith; iv) optionally diluting the blood sample in a carrier fluid; v) loading the blood sample at a sample application location on the monolith, wherein the monolith is sized to absorb the flow of the blood sample along its length or radius, and wherein the flow comprises a) a first fraction of the blood sample comprising blood cells and blood-cell-free fluid wicking into a first zone of the monolith; and b) a second fraction of the blood sample free of blood cells wicking through the first zone of the monolith, into a second zone of the monolith and into the reagent zone of the monolith; vi) waiting for the blood-cell-free fraction to wick into the reagent zone, wherein the blood-cell-free fraction mixes with the reagent in the reagent zone; vii) optionally mechanically separating the first (blood cell-containing) zone from the monolith; viii) optionally loading a chase fluid at the sample application location or at another location on the monolith; ix) adjusting the temperature of the mixture in the reagent zone to promote amplification of the target, provided the amplification reagent and target nucleic acid are present in the reagent zone; x) waiting for the amplification of the target nucleic acid and/or amplification of a signal; xii) detecting the presence or absence of an indicator or indicator system in the reagent zone of the monolith, corresponding to the presence or absence of the target nucleic acid; and xiii) optionally mechanically separating the reagent zone from the monolith. In one aspect of the foregoing method, the amplifying is performed using a polymerase chain reaction (PCR); an isothermal nucleic acid amplification; a signal amplification method; or a nucleic acid amplification and a signal amplification. In one aspect of the foregoing method, the target nucleic acid originates from herein the target nucleic acid originates from bacteria, viruses, fungi, unicellular eukaryotes or other parasitic organisms, or cell(s) originating from the host organism, including transplanted cells, tumor cells, free circulating nucleic acids or circulating nucleic-acid-containing biomolecules.

Also provided are methods for detecting target nucleic acid in a blood-cell-free fraction of a blood sample, comprising: i) providing a monolith fabricated according to the methods described herein; wherein at least one zone of the monolith is designated as a reagent zone; ii) optionally diluting the blood sample in a carrier fluid; iii) loading the blood sample at a sample application location on the monolith, wherein the monolith is sized to absorb the flow of the blood sample along its length or radius, and wherein the flow comprises a) a first fraction of the blood sample comprising blood cells and blood-cell-free fluid wicking into a first zone of the monolith; and b) a second fraction of the blood sample free of blood cells wicking through the first zone of the monolith, into a second zone of the monolith and not into the reagent zone of the monolith; iv) waiting for the blood-cell-free fraction to wick into the second zone of the monolith; v) optionally mechanically separating the first zone from the monolith; vi) loading at least one amplification and/or detection reagent for a target nucleic acid into an initially dry reagent zone of the monolith, wherein the reagent wicks into the second zone of the monolith and wherein the reagent mixes with the blood-cell-free fraction in the second zone; vii) optionally loading a chase fluid at the sample application location or at another location on the monolith; viii) adjusting the temperature of the mixture in the second zone to promote amplification of the target, provided the amplification reagent and target nucleic acid are present in the second zone; ix) waiting for the amplification of the target nucleic acid and/or amplification of a signal; and x) detecting the presence or absence of an indicator or indicator system in the monolith, corresponding to the presence or absence of the target nucleic acid. In one aspect of the foregoing method, the amplifying is performed using a polymerase chain reaction (PCR); an isothermal nucleic acid amplification; a signal amplification method; or a nucleic acid amplification and a signal amplification. In one aspect of the foregoing method, the target nucleic acid originates from bacteria, a virus, a fungus, a unicellular eukaryote or a cell-free nucleic acid.

Also provided are methods for fractionating a blood sample into blood cells and a blood-cell-free fraction, comprising i) providing a monolith fabricated according to the methods described herein; ii) providing a subsequent wicking device; iii) coupling the subsequent wicking device into fluidic communication to at least one surface of the monolith; iv) optionally diluting the blood sample in a carrier fluid; v) loading the blood sample at a sample application location on the monolith, wherein the monolith is sized to absorb the flow of the blood sample along its length or radius, and wherein the flow comprises a) a first fraction of the blood sample comprising blood cells and blood-cell-free fluid wicking into the monolith; and b) a second fraction of the blood sample free of blood cells wicking through the monolith and into the subsequent wicking device; vi) optionally loading a chase fluid at the sample application location or at another location on the monolith; vii) waiting for the blood-cell-free fraction to wick into the subsequent wicking device of the monolith; and viii) optionally uncoupling the wicking device from the monolith. In one aspect of the foregoing method, the wicking device is another polymer monolith or a nitrocellulose strip.

Also provided herein is a lateral flow porous monolith for the fractionation of a blood sample into blood cells and a blood-cell-free fraction, comprising a porous organic polymer monolith operable without the assistance of fluidic devices, wherein the monolith is sized to absorb the flow of the blood sample along at least a portion of its length or radius and the monolith is configured to i) wick the blood sample into the monolith; ii) sequester the blood cells from the blood sample in a first zone; iii) wick the blood-cell-free fraction of the blood sample through the first zone and optionally into a second zone of the monolith; and iv) have a measured red blood cell retention factor (Rf) value in the range of 0.01 to 0.8. In one aspect of the foregoing method, the monolith further comprises a plurality of inorganic beads coated with an organic porous polymer coating, wherein the inorganic beads are comprised of silica, metals or metal oxides. In one aspect of the foregoing method, the monolith is a self-wicking monolith with a two minute water wick rate between 1.5 and 5.0 centimeters. In one aspect of the foregoing method, the monolith has a pore size within a range of 2-7 microns. In one aspect of the foregoing method, the monolith has a porosity of 50 to 85 percent. In one aspect of the foregoing method, the monolith is a lateral flow monolith. In one aspect of the foregoing method, the monolith comprises a reagent zone configured to receive a blood-cell-free fraction of a blood sample that has wicked through the first zone and optionally into a second zone of the monolith. In one aspect of the foregoing method, the monolith further comprises a subsequent wicking device, wherein the lateral flow device is another polymer monolith or a nitrocellulose strip and wherein the wicking device is configured to i) be selectively coupled to the lateral flow porous monolith; ii) be loaded in at least a portion of the wicking device with at least one amplification and/or detection reagent for a target nucleic acid, and iii) receive a blood-cell-free fraction of a blood sample that has wicked through at least the first zone of the lateral flow porous monolith and into the wicking device. In one aspect of the foregoing method, the monolith has a minimum tensile strength corresponding to supported weight of 10 grams according to the method of FIG. 14.

Also provided are methods for fabricating multilayer porous polymer monoliths as described herein in a pipette tip. These methods comprise e.g., i) providing a pipette tip having a conical cavity with an opening at the top, and the narrower end of the pipette is sealed liquid-tight, wherein the wall of the pipette tip is transparent to the passage of UV light, provided UV light is used to initiate polymerization; ii) dispensing into the pipette tip a first polymerizable composition comprising a mixture of a plurality of monomers and a porogenic solvent; iii) dispensing into the pipette tip a second polymerizable composition comprising a mixture of a plurality of monomers and a porogenic solvent; iv) optionally providing a source of UV light directed from a plurality of light sources positioned adjacent to the sides of the pipette tip from a plurality of respective directions to provide a uniform source of UV light directed towards the polymerizable compositions in the pipette tip; and v) initiating polymerization of the polymerizable compositions in the pipette tip.

In some aspects, polymerization in the aforementioned methods is initiated through electromagnetic radiation, chemical reaction, via heat, or combinations thereof. In other aspects of the aforementioned method, the volumetric mass density of the first polymerizable composition is greater than the volumetric mass density of the second polymerizable composition.

Also provided herein are molds for the fabrication of multilayer porous monoliths as described herein. These methods comprise e.g., i) a mold part comprising a sheet having first and second sides, configured with a hollow inner cavity with an opening at the upper end for receiving a plurality of polymerizable compositions; and ii) a first and a second sheet, each having inner and outer flat surfaces, each sheet sized to a length and width to enclose the hollow inner cavity of the mold part when the first and second sheets are clamped on opposite sides of the mold part, wherein the first and second sheets are transparent to the passage of UV light, provided UV light is used to initiate polymerization of the polymerizable compositions.

In some aspects, the inner surfaces of the first and second sheets described in the aforementioned method comprise non-stick surfaces. In other aspects, the aforementioned method further comprises a non-stick transparent layer applied to the inner surfaces of the first and second sheets. Non-stick transparent layers include, but are not limited to, those that comprise a layer of polyethylene, a layer of polyvinyl chloride (PVC), polypropylene, or other polyolefin polymer or a spray on layer of polytetrafluoroethylene (PTFE).

Other methods of fabricating multilayer porous polymer monoliths in a mold comprise i) a mold part comprising a sheet having first and second sides, configured with a hollow inner cavity with an opening at the upper end for receiving a plurality of polymerizable compositions; ii) a first and a second sheet, each having inner and outer flat surfaces, each sheet sized to a length and width to enclose the hollow inner cavity of the mold part when the first and second sheets are clamped on opposite sides of the mold part, wherein the first and second sheets are transparent to the passage of UV light, provided UV light is used to initiate polymerization of the polymerizable compositions; iii) dispensing into the hollow cavity of the mold a first polymerizable composition comprising a mixture of a plurality of monomers and a porogenic solvent; iv) dispensing into the hollow cavity of the mold a second polymerizable composition comprising a mixture of a plurality of monomers and a porogenic solvent; v) optionally providing a source of UV light directed from a plurality of light sources positioned adjacent to the outer surfaces of the first and second sheets to provide a source of UV light directed towards the polymerizable compositions in the cavity of the mold; and vi) initiating polymerization of the polymerizable compositions in the cavity of the mold. In other aspects of the aforementioned method, the volumetric mass density of the first polymerizable composition is greater than the volumetric mass density of the second polymerizable composition.

In some aspects, polymerization in the aforementioned methods is initiated through electromagnetic radiation, chemical reaction, via heat, or combinations thereof.

Other monoliths and processes included in the present disclosure are as described in the Exemplification section below. The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

EXEMPLIFICATION

FIG. 1 shows a view of a lateral flow porous polymer monolith 110 for processing blood sample 102 as it is applied at sample application location 112 close to one end of monolith 110. At the opposite end of monolith 110, optionally dry reagent 120 is stored in reagent zone 118. Monolith 110 is a porous polymer monolith with self-wicking properties and can fractionate a blood sample into blood cells and a blood-cell-free (BCF) fraction. Reagent 120 is at least one amplification and/or detection reagent to be used to process a BCF fraction after it wicks into reagent zone 118. Reagent 120 will amplify a target nucleic acid in the BCF fraction, if present, and provide an indication if the target nucleic acid is present. Blood sample 102 can optionally be diluted by am isotonic solution, such as phosphate buffered saline or other buffers. The volume of blood sample 102 should be selected to correlate with the effective loading volume of a particular monolith 110 so that the BCF fraction can wick into the reagent zone 118.

Porous polymer monoliths can be formed by mixing monomers and porogenic solvents to form a polymerizable composition and initiation of polymerization, which may be done using heat, UV light, or generation of radical species by chemical reaction. Monoliths for fractionating blood can be characterized by having a highly porous structure, a distribution of certain pore sizes, a wicking rate within a certain range and a red blood cell retention factor (Rf) within a specific range.

Figure 2:
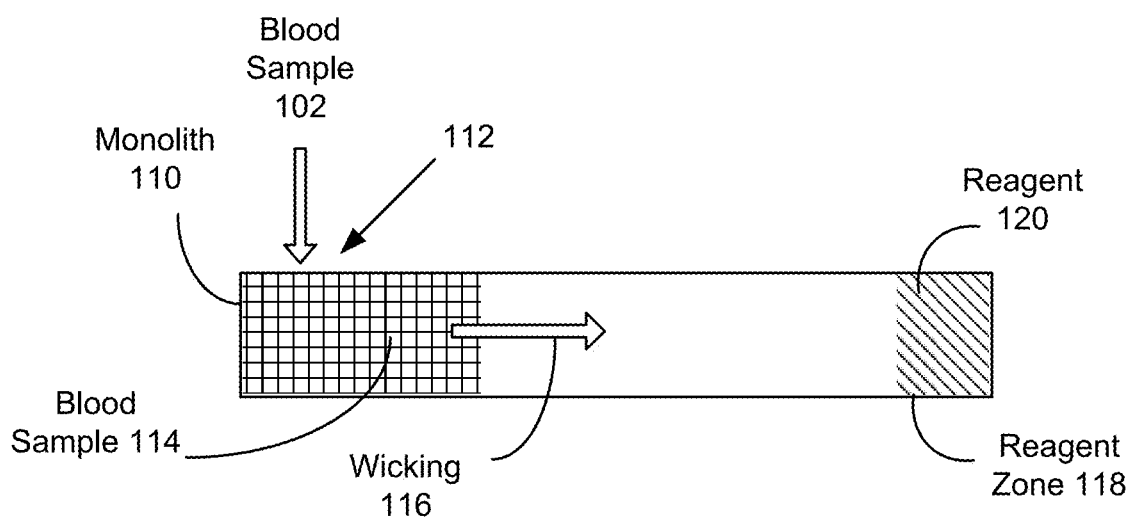
FIG. 2 shows a view of a monolith as it begins to process a blood sample

FIG. 2 shows a view of monolith 110 of FIG. 1 as it begins to process blood sample 102. Blood sample 102 has entered monolith 110 via sample application location 112 and a portion 114 of blood sample 102 is wicking through monolith 110 in the direction shown by arrow 116.

Figure 3:
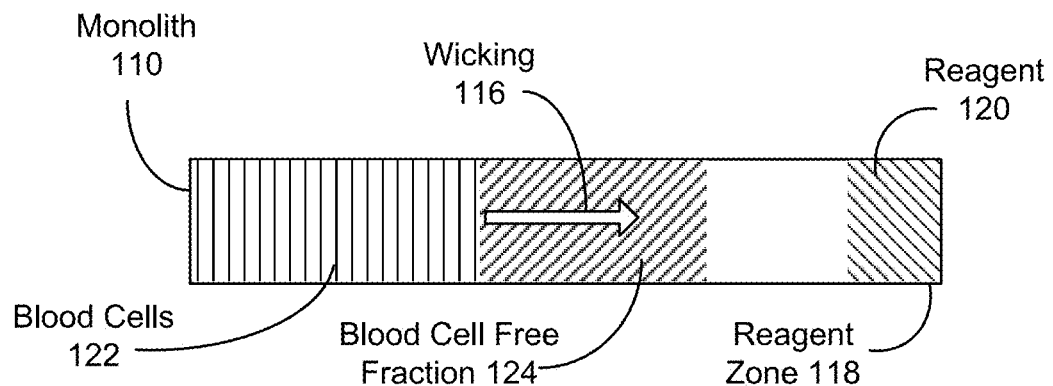
FIG. 3 shows a view of a monolith as fractionation of a blood sample begins.

FIG. 3 shows a view of monolith 110 of FIG. 1 as fractionation of a blood sample 102 is taking place. Blood cells 122 that were in blood sample 102 are being sequestered in the first zone of monolith 110. The remaining portion of blood sample 102, i. e., the BCF fraction 124 is being wicked further into monolith 110 and towards reagent zone 118.

Figure 4:
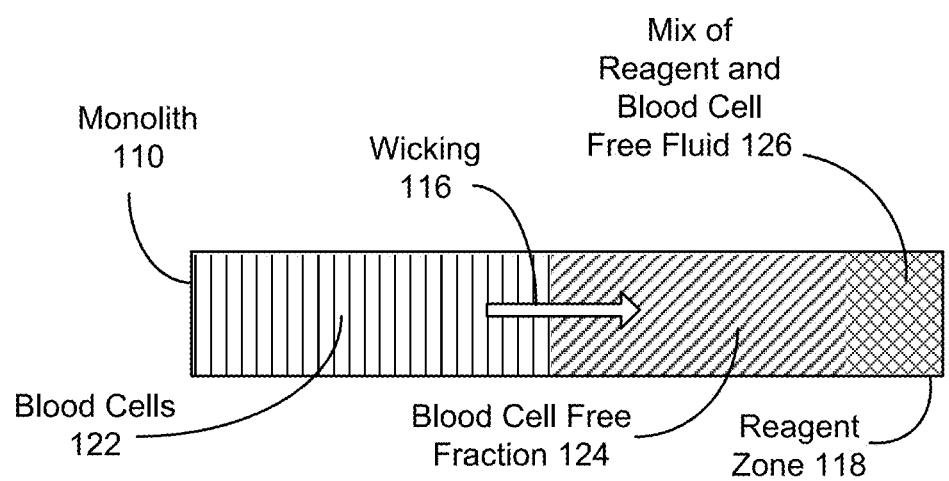
FIG. 4 shows a view of a monolith as the blood-cell-free fraction of the blood sample enters the reagent zone.

FIG. 4 shows a view of monolith 110 of FIG. 1 as monolith 110 has fractionated BCF fluid 124 from the blood sample 102 and the BCF fraction 124 has entered reagent zone 118. Reagent zone 118 has been loaded with reagent 120 to provide the chemicals needed to perform amplification and/or detection of a target nucleic acid. The reagent 120 is preferably in a dried form in reagent zone 118. Bloods cells 122 have been sequestered in a portion of monolith defining a first zone. Blood cells 122 have not been damaged or lysed by the action of wicking through into monolith 110. The portion of monolith 110 into which BCF fraction 124 has wicked defines a second zone. That second zone containing BCF fraction 124 extends into and overlaps with reagent zone 118.

BCF fluid 124 mixes with reagent 120 in reagent zone 118 forming a mixture 126. If the target nucleic acid is present in the BCF fluid 124 then amplification can take place of the target nucleic acid, thereby increasing the number of copies of the target nucleic acid. Various amplification methods are known in the field, such as a polymerase chain reaction (PCR) and isothermal amplification that can be used to increase the number of copies of the target nucleic acid, and thus facilitate the detection of the target nucleic acid, if present.

Some known amplification methods include loop mediated isothermal amplification process (LAMP), Recombinase/Polymerase Assay (RPA), Strand Displacement Amplification (SDA), NASBA, Multiple Displacement Amplification (MDA), Rolling Circle Amplification (RCA), Ligase Chain Reaction (LCR), Helicase Dependent Amplification (HDA) and Ramification (RAM). Signal amplification methods are known in the field, such as branched DNA (bDNA) and Hybrid Capture.

Various detection methods are known in the field, such as quenching of unincorporated amplification signal reporters (QUASR), quantitative polymerase chain reaction (qPCR), Nicking Endonuclease Signal Amplification (NESA) and Enzyme-linked Immunosorbent Assay (ELISA). QUASR is described in Ball, C. S. et al, Quenching of Unincorporated Amplification Signal Reporters in Reverse-Transcription Loop-Mediated Isothermal Amplification Enabling Bright, Single-Step, Closed-Tube, and Multiplexed Detection of RNA Viruses, Analytical Chemistry, 2016, 88, 3562-3568, Mar. 16, 2016.

Figure 5:
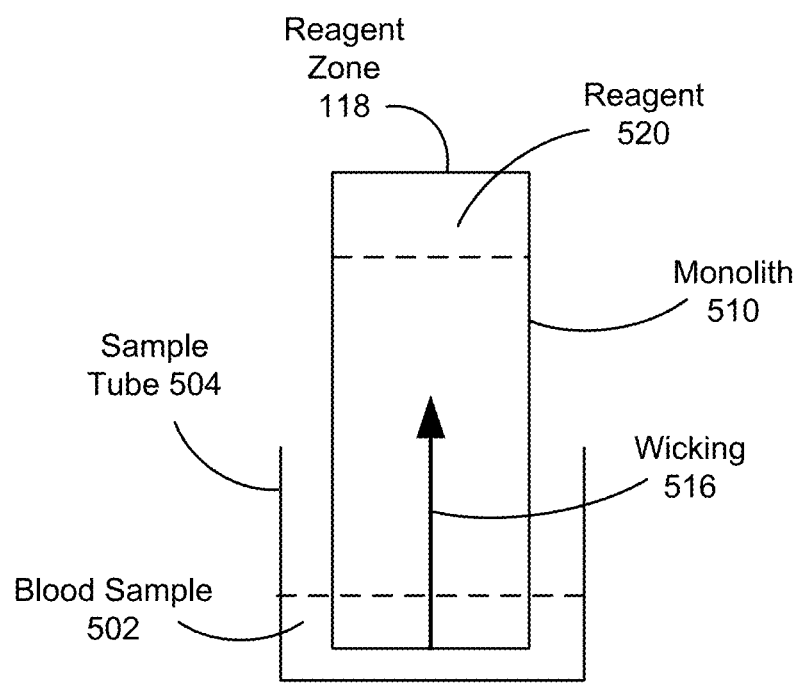
FIG. 5 shows a cross sectional view of a sample tube with a blood sample into which a monolith has been inserted.

FIG. 5 shows a lateral view of sample tube 504 with blood sample 502 into which monolith 510 has been inserted. At the upper end of monolith 510 there is a reagent zone 518 containing reagent 520. When the bottom end of monolith 510 is inserted in blood sample 502, then blood sample 502 starts wicking up into monolith 510 in the wicking direction shown by arrow 516.

As blood sample 502 wicks into monolith 510, the blood cells in blood sample 502 will be sequestered in the bottom portion of monolith 510. The BCF fraction of blood sample 502 will continue wicking further up into monolith 510 and will enter reagent zone 518. If the target nucleic acid is present in the BCF fraction, then amplification of the target nucleic acid will take place and then the detection of the target nucleic acid will be evident via an indicator or indication system.

Indication methods can utilize one or more of many known physical phenomena that comprise molecules that are: light-absorbing, chromogenic, fluorescent (to include provision for fluorescence, time-resolved fluorescence, fluorescence polarization, and/or Firster Resonance Energy Transfer [FRET]), phosphorescent, luminescent, radioactive, or other molecules that absorb and/or emit electromagnetic and/or nuclear radiation. Other available indication systems are dependent on electrochemical changes in the reagent zone, such as changes in conductivity.

Figure 6:
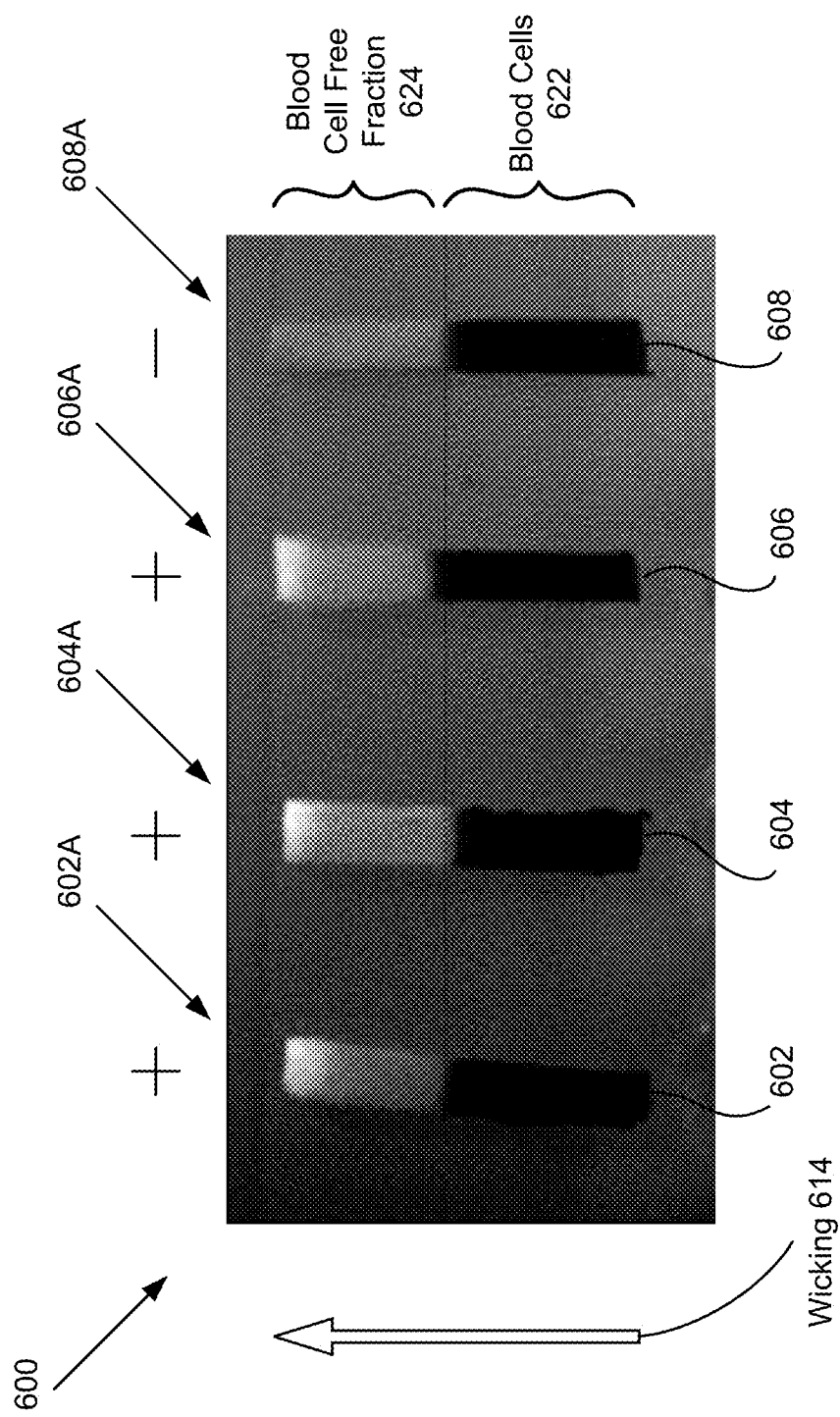
FIG. 6 is a photo of four monoliths configured to amplify and detect a target nucleic acid, if present.

FIG. 6 shows a photo 600 of four monoliths 602, 604, 606 and 608. A blood sample containing a flu virus has been applied to the bottom portion of monoliths 602, 604, and 606. A blood sample without a flu virus has been applied to the bottom portions of monolith 608 as a control. In monoliths 602, 604, 606 and 608 the blood cell portions 622 has been sequestered in the lower half of each of the monoliths shown. Wicking of the blood samples has proceeded from the bottom to the top of each monolith in the upward direction as shown by arrow 614.

In monoliths 602, 604, 606 and 608, the BCF fraction 624 has continued to wick into the upper half of the monoliths. Each of the monoliths at the upper end has a reagent zone for the storage of at least one reagent for amplification and/or detection of a target nucleic acid. As the BCF fraction of each blood sample enters the reagent zone of each respective monolith, then the amplification and detection reagent will process the BCF fraction and provide an indication if the target nucleic acid is present. The amplification and detection reagent used was a LAMP QUASR reagent. FIG. 6 shows that monoliths 602, 604 and 606 each received a blood sample which was fractionated and from which the target nucleic acid was amplified. The indicator system in each generated a visually observable indication 602A, 604A and 606A of detection of the target nucleic acid that originated from a flu virus in this example. The lack of a visible indicator at the upper end 608A of monolith 608 indicates that the target nucleic acid was not present in the control monolith 608.

The polymerizable composition used to fabricate the self-wicking porous polymer fractionating monolith in FIG. 6 included the following mix of monomers (25% v:v): EGDMA—70%, TEGDA—10%, TMP(EO)TA—10% and HEMA—10%; and the following mix of solvents (75% v:v): 1-Octanol ($C_8H_{10}O$)—60% and Methanol ($CH_4O$)—40%.

Figure 7:
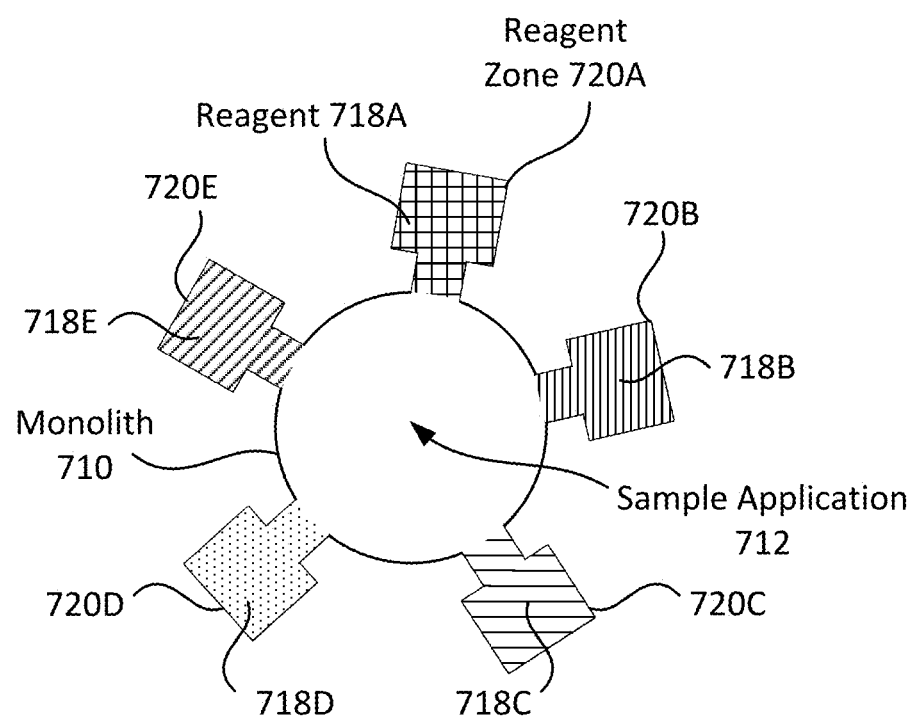
FIG. 7 shows a top view of a monolith with five reagent zones.

FIG. 7 shows a top view of monolith 710 configured with a sample application location 712 in its center. Monolith 710 has five reagent zones 718A-718E. FIG. 7 is an embodiment that can process a blood sample that will wick radially outward from the center of monolith 710. As the blood sample wicks away from the center, the blood cells contained in the blood sample will be sequestered in the center of monolith 710. Monolith 710 can provide for the detection of target nucleic acids in up to five different target nucleic acids. As the BCF fraction wicks away from the center and towards the perimeter of monolith 710, the BCF fraction will be subdivided into five portions and mixed with the respective five reagents 720A-720E.

Figure 8:
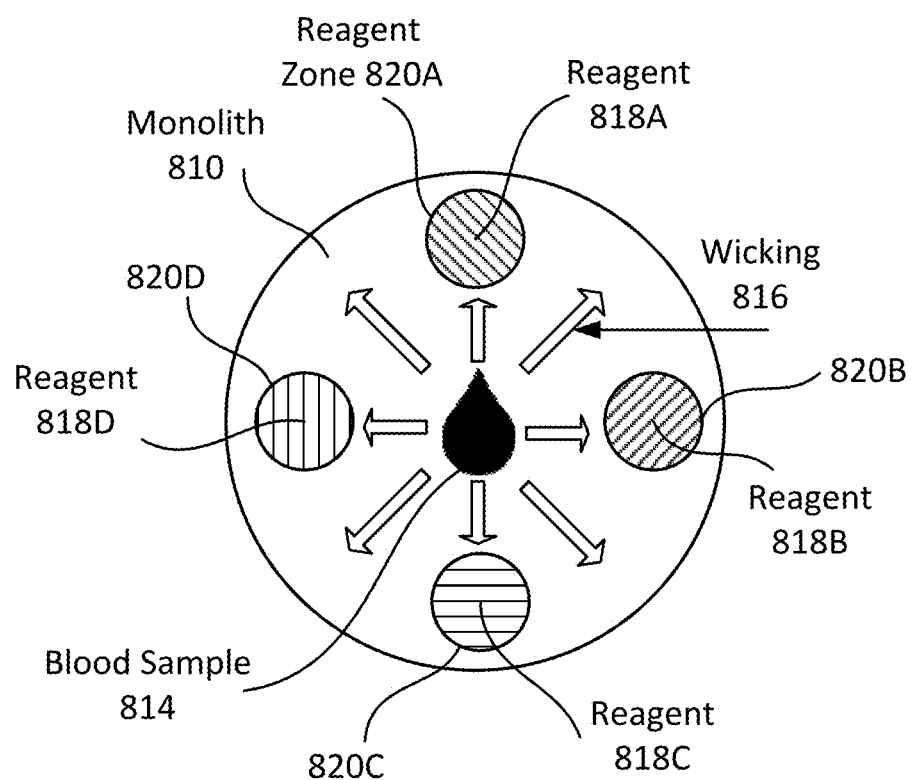
FIG. 8 shows a top view of a disc shaped monolith with four reagent zones.

FIG. 8 shows a top view of a disc shaped monolith 810 with four reagent zones 818A-818D with respective reagents 820A-820D. Monolith 810 provides for the testing of blood sample 814 to detect up to four different target nucleic acids. Blood sample 814 is applied in the center of monolith 810 and the blood sample proceeds to wick from the center of monolith 810 towards the perimeter as shown by arrows 816.

Figure 9:
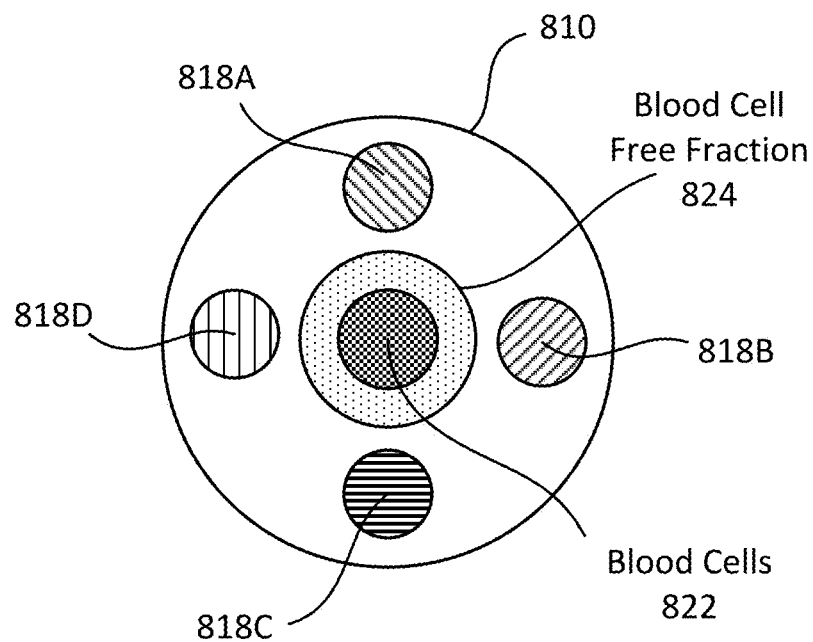
FIG. 9 shows a top view of a monolith as blood cells are sequestered in the center of the monolith and as blood-cell-free fluid wicks away from the center towards the perimeter of the monolith.

FIG. 9 shows a top view of monolith 810 as blood cells 822 are sequestered in the center of monolith 810 and as BCF fluid 824 wicks away from the center towards the perimeter of monolith 810.

Figure 10:
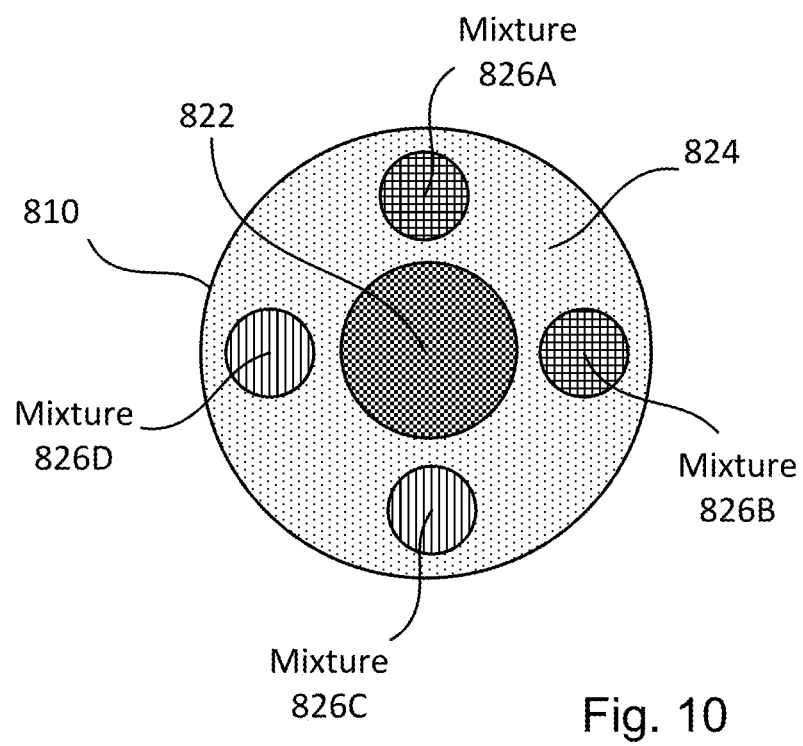
FIG. 10 shows a top view of a monolith as the blood-cell-free fluid has proceeded to wick to the perimeter of monolith.

FIG. 10 shows a top view of monolith 810 as the blood cells 822 have been sequestered in the center of monolith 810 and the BCF fluid 824 has proceeded to wick to the perimeter of monolith 810. BCF fluid 824 has also entered reagents zones 818A-D where the fluid 824 is able to react with up to four different reagents 820A-D and resulting in respective mixtures 826A-D. If each of the target nucleic acids is present in blood sample 814, then an indication will become evident in each of the reagent zones.

Figure 11:
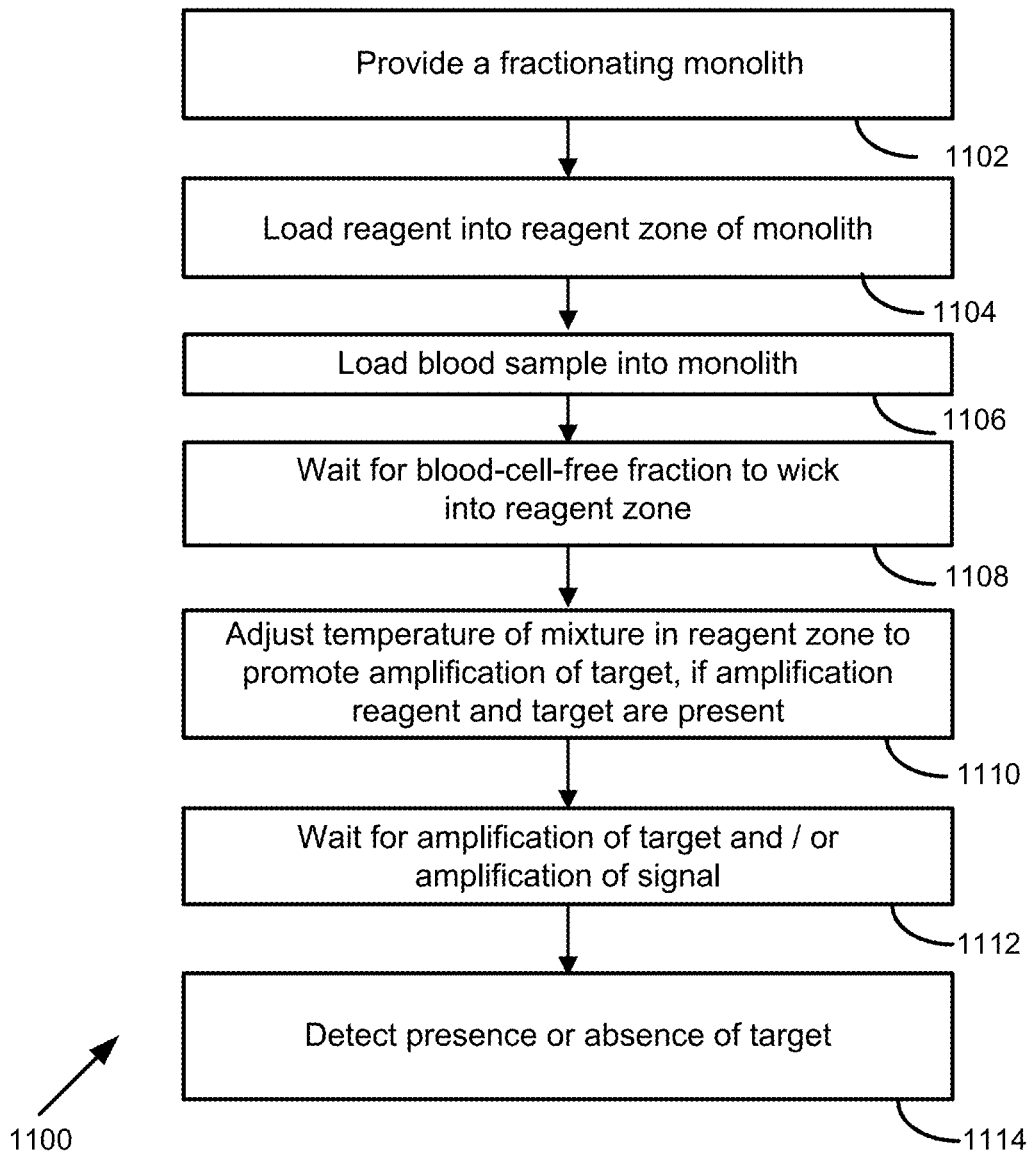
FIG. 11 shows a flowchart for a method of fractionating a blood sample and the amplification and/or detection of a target nucleic acid.

FIG. 11 shows a flowchart for a method 1100 of fractionating a blood sample and the detection of a target nucleic acid. This method corresponds to the processing of a blood sample as described with respect to FIGS. 1-10. In block 1102, a monolith is provided for the processing of the blood sample. The dimensions of the monolith are selected to be able to absorb, along its length or radius, the volume of the blood sample to be applied. In block 1104, at least one amplification and/or detection reagent for a target nucleic acid is loaded into the reagent zone of the monolith. After step 1104, an option is to dry the at least one reagent in the monolith.

In block 1106, the blood sample to be tested is loaded into the monolith at the sample application location. Prior to loading the blood sample, an option is to dilute the blood sample with an appropriate carrier fluid, such as phosphate buffered saline. The fractions of the blood sample comprising blood cells and BCF fluid may wick into a first zone of the monolith and a first fraction comprising blood cells may be sequestered in the first zone; and a second fraction of the blood sample free of blood cells comprising BCF fluid may wick through the first zone of the monolith, into a second zone of the monolith, and into the reagent zone of the monolith.

In block 1108, a certain amount of time will elapse while waiting for the BCF fraction to wick into the reagent zone, the BCF fraction mixing with the reagent in the reagent zone. The amount of time will depend on many factors, including the size and shape of the monolith, the volume of the blood sample applied to the monolith, and the wicking rate through the monolith. This waiting time can be determined for a particular fractionating monolith prior to use. In other words, the waiting time is pre-determined as in waiting a predetermined time period. An option after step 1108 is to mechanically separate the first (blood cell-containing) zone from the monolith. Another option is to load a chase fluid at the sample application location or at another location on the monolith, to help wick the blood sample through the monolith.

In block 1110, depending on the type of amplification method that is used, the temperature of the mixture in the reagent zone is adjusted to promote amplification of the target if the amplification reagent and target nucleic acid are present in the reagent zone. If, for example, an isothermal amplification method is being used, the temperature in the reagent zone must be raised above room temperature. If a PCR method is being used, then a certain amount of thermal cycling must take place.

Elevated temperatures required for nucleic acid amplification will generally result in cell lysis or viral particle lysis. Therefore, it is important that bulk fluid flow has completed or is near completion before heat-induced cell or particle lysis. Because lysed red cells contribute the majority of amplification and detection inhibitors, it is important that the red cells or their lysis products are sufficiently distant so that the diffusion of inhibitors from these cells into the detection zone is minimal during the time course of the test. By contrast, the lysis of non-blood cells or particles (e.g. bacteria, viruses) at or near the reagent zone may be advantageous if their nucleic acids are targets for amplification and/or detection.

In step 1112, a certain amount of time will elapse while waiting for the amplification of a target nucleic acid to take place if the target is present in the mixture in the reagent zone. If the target is not present, then the waiting must have an upper limit on how long to wait before seeing or sensing in the subsequent detecting step 1114 that the target is not detected. This time period will depend on many factors, but can be determined for a particular fractionating monolith and application.

In step 1114, the detection, i.e., the presence or absence of an indicator or indication system in the reagent zone of the monolith, can be determined by visual, optical or other indicative methods, corresponding to the presence or absence of the target nucleic acid in the blood sample. An option after step 1114 is to mechanically separate the reagent zone from the monolith.

Figure 12:
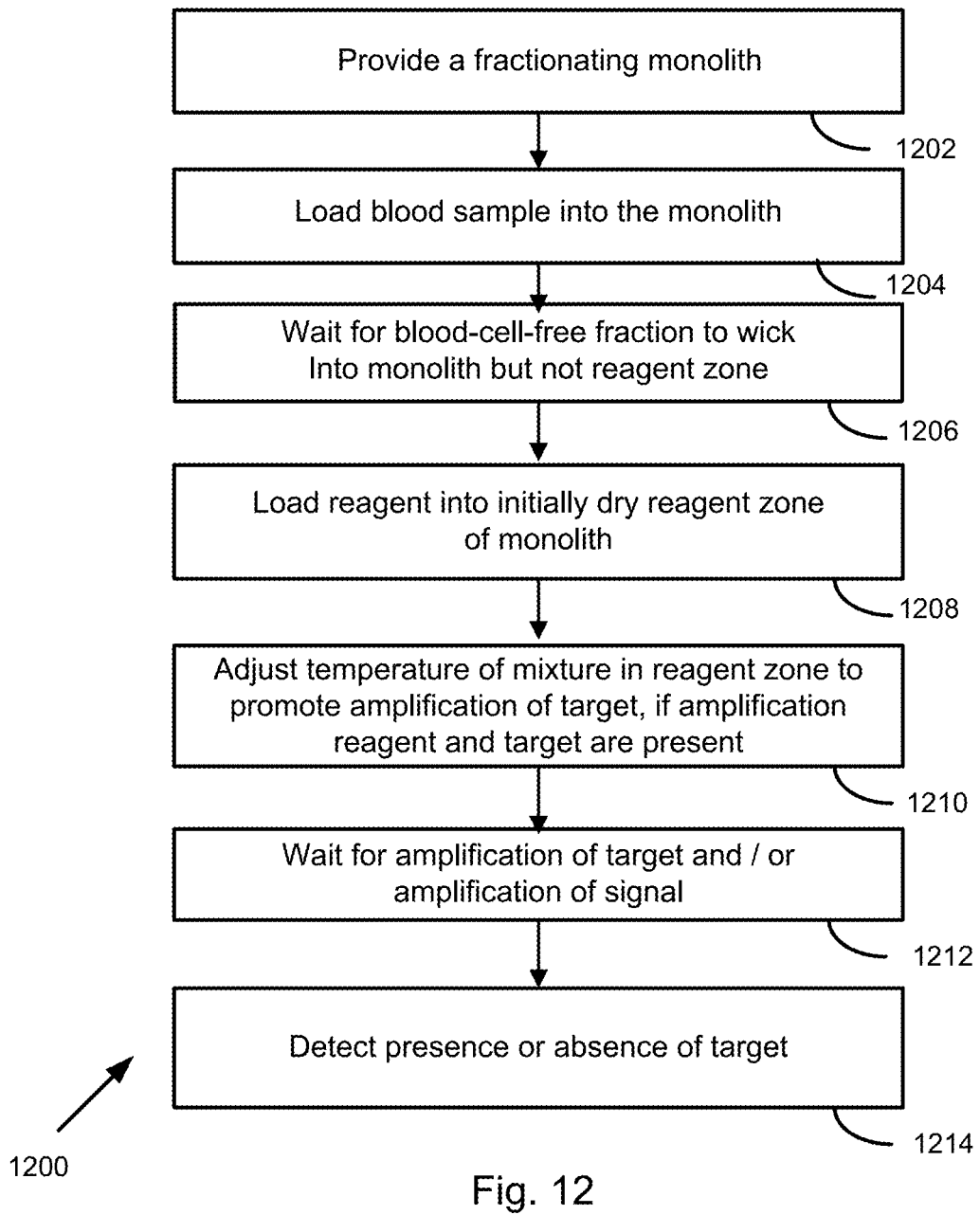
FIG. 12 shows a flowchart for another method of fractionating a blood sample and the amplification and/or detection of a target nucleic acid.

FIG. 12 shows a flowchart for a method 1200 of fractionating a blood sample and the detection of a target nucleic acid. In step 1202, a monolith is provided for the processing of the blood sample. The dimensions of the monolith are selected to be able to absorb, along its length or radius, the volume of the blood sample to be applied. In step 1204, the blood sample to be tested is loaded into the monolith at the sample application position. The blood sample comprising blood cells and BCF fluid may wick into a first zone of the monolith and the blood cells will be sequestered in the first zone. A second fraction of the blood sample free of blood cells comprising BCF fluid may wick through the first zone of the monolith, into a second zone of the monolith and not into the reagent zone of the monolith. As a result, the reagent zone of the monolith remains dry during this step. Prior to loading the blood sample, an option is to dilute the blood sample with an appropriate carrier fluid, such as phosphate buffered saline or other buffers.

In step 1206, a certain amount of time will elapse while waiting for the BCF fraction to wick into the second zone of the monolith. The amount of time will depend on many factors, including the size and shape of the monolith, the volume of the blood sample applied to the monolith, and the wicking rate through the monolith. This waiting time can be determined for a particular fractionating monolith prior to use. An option after step 1206 is to mechanically separate the first (blood cell-containing) zone from the monolith.

In step 1208, at least one amplification and/or detection reagent for a target nucleic acid is loaded into an initially dry reagent zone of the monolith; the reagent wicks through the reagent zone and into the second zone of the monolith; the reagent mixing with the BCF fraction in the second zone. After step 1208, an option is to load a chase fluid at the sample application location or at another location on the monolith, to help wick the blood sample through the monolith.

In step 1210, depending on the type of amplification method that is used, the temperature of the mixture in the second zone is adjusted to promote amplification of the target if the amplification reagent and target nucleic acid are present in the second zone. If, for example, an isothermal amplification method is being used, the temperature in the reagent zone must be raised above room temperature. If a PCR method is being used, then a certain amount of thermal cycling must take place.

In step 1212, a certain amount of time will elapse while waiting for the amplification of a target nucleic acid to take place if the target is present in the mixture in the reagent zone. If the target is not present, then the waiting time must have an upper limit as to how long to wait before seeing or sensing in the subsequent detecting step 1214 that the target is not detected. This time period will depend on many factors, but can be determined for a particular fractionating monolith and application.

In step 1214, the detection, i.e. the presence or absence of an indicator or indication system in the reagent and/or second zones of the monolith, can be determined by visual, optical or other indicative methods, corresponding to the presence or absence of the target nucleic acid in the blood sample.

Figure 13:
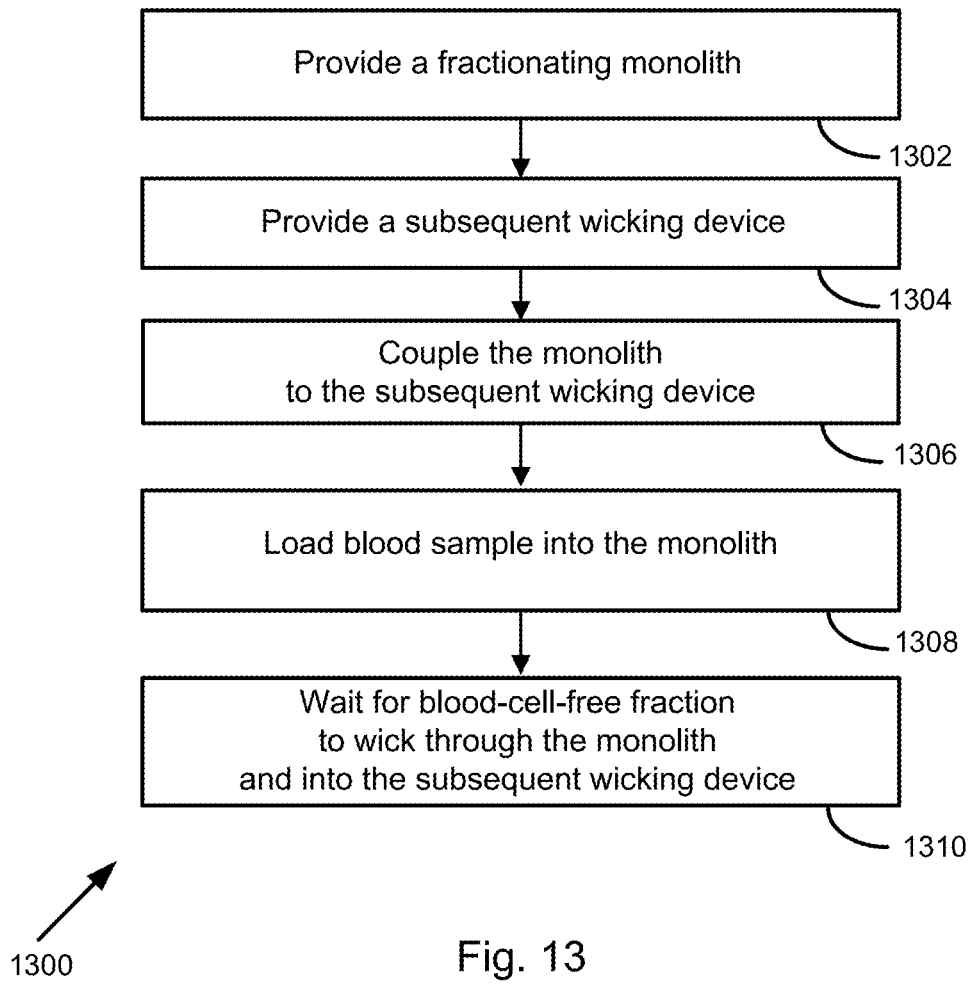
FIG. 13 shows a flowchart for a method of fractionating a blood sample and the wicking of a blood-cell-free fraction into a subsequent wicking device coupled to a monolith.

FIG. 13 shows a flowchart for a method 1300 of fractionating a blood sample into blood cells and a BCF fraction. In step 1302, a fractionating monolith is provided for the processing of the blood sample. In step 1304, a subsequent wicking device is provided. In step 1306, the wicking device is coupled into fluidic communication with at least one surface of the monolith.

In step 1308, the blood sample to be tested is loaded at the sample application position into the monolith. The blood sample comprising blood cells and BCF fluid may wick into the monolith and a first fraction of the blood sample comprising blood cells will be sequestered in the monolith. A second fraction of the blood sample free of blood cells comprising BCF fluid may wick through the monolith and into the subsequent wicking device. Prior to loading the blood sample, an option is to dilute the blood sample with an appropriate carrier fluid, such as phosphate buffered saline or other buffers.

In step 1310, a certain amount of time will elapse while waiting for the BCF fraction to wick into the wicking device. The amount of time will depend on many factors, including the size and shape of the monolith, the size and shape of the wicking device, the volume of the blood sample applied to the monolith, the wicking rate through the monolith, and the wicking rate in the wicking device. This waiting time can be determined for a particular combination of fractionating monolith and wicking device prior to use. An option after step 1310 is to uncouple the wicking device from the monolith.

Figure 14:
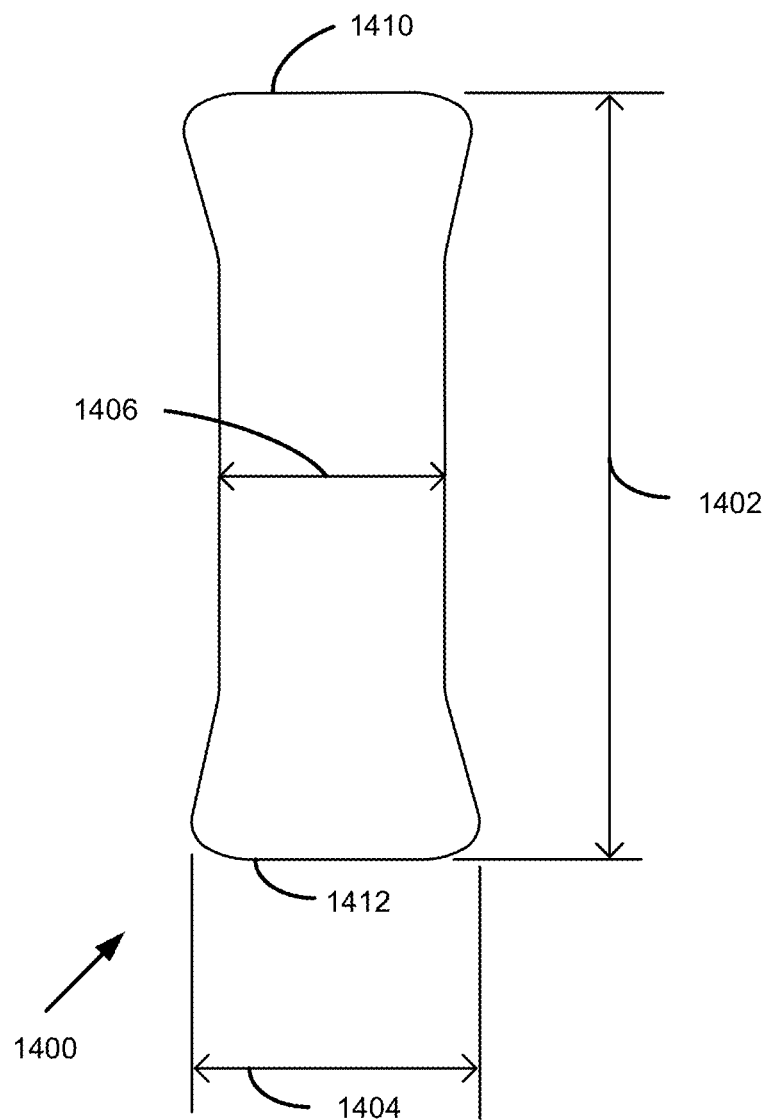
FIG. 14 shows a view of a monolith used for testing the tensile strength of the monolith.

FIG. 14 shows a view of a monolith 1400 with a length 1402 and a width 1404 at the widest portions used for testing the tensile strength of various formulations of a fractionating monolith. A fractionating monolith must have some minimum tensile strength in order to be manufactured, transported and used for fractionating. A standardized tensile test, similar to a test such as the ASTM E8 (or ASTM D638) tensile test was developed. Monolith 1400 was fabricated with a "dog bone" shape, being narrower at the center 1406 than at the upper end 1410 and lower end 1412. After fabrication using a particular formula of monomers and solvents, after any remaining solvent had been washed out and the monolith had been dried and stored at room temperature for a time period, the monolith was ready to be tested. The particular standardized dimensions of a monolith under test was 6.35 mm in length, 19.05 mm at the two ends, 12.7 mm at the center and 1.0 mm+/−0.1 mm in thickness. The upper end of a monolith 1400 under test was clamped at the top end 1410 and a series of increasing weights, starting at 10 grams were attached and increasing amounts of weight were added until the monolith under test was pulled apart in the narrower section of the monolith. It was determined that a fractionating monolith had to have a minimum strength of 10 grams in this test in order to be durable enough to undergo the expected handling conditions prior to and during a test for a target.

Fractionating lateral flow monoliths can be formed by mixing together monomers and porogenic solvents to form a polymerizable composition by providing a mixture of monomers, such as at least one monomer and at least one radically polymerizable trimethylolpropane (TMP)-based monomer having the formula:

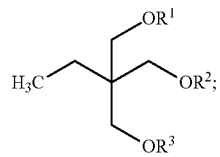

wherein $R^1$, $R^2$, and $R^3$ are each independently selected from —(CH$_2$CH$_2$O)$_n$H, —CH$_2$CH$_2$O)$_n$C(O)CH$_2$CH$_2$SH, —(CH$_2$CH$_2$O)$_n$C(O)CH═CH$_2$, and —(CH$_2$CH$_2$O)$_n$C(O)C(CH$_3$)═CH$_2$; and each n is independently an integer from 0 to 12, wherein said (TMP)-based monomer is present in an amount ranging from 0.1% to 44% (v:v) of the total volume of the plurality of monomers. One version of the TMP-based monomer is when n=3. One version of a TMP-based monomer is TMP(EO)TA (trimethylolpropane ethoxy triacrylate) from 0.1% to 44%. TMP(EO)TA as one monomer in a mixture used to make a fractionating porous polymer monolith can increase the strength of such a monolith. TMPMP (trimethylolpropane tris(3-mercaptopropionate)) from 0% to 7% (v:v) is another example of a monomer in a mixture used to make a fractionating porous polymer monolith which can increase the flexibility of such a monolith. Other monomers for making fractionating monoliths include: EGDMA (ethylene glycol dimethacrylate) from 34% to 75% (v:v), HEMA (2-hydroxyethyl methacrylate) from 10% to 35% (v:v), TEGDA (tetra(ethylene glycol) diacrylate) from 0% to 15% (v:v) and TEGDMA (tetra(ethylene glycol) dimethacrylate) from 0% to 20% (v:v).

A lateral flow porous monolith for the fractionation of a blood sample into blood cells and a BCF fraction may include a porous organic and optionally inorganic polymer monolith operable without the assistance of fluidic devices. Such a monolith may be sized to absorb the flow of the blood sample along at least a portion of its length or radius. A fractionating monolith may be configured to: load the blood sample into the monolith; wick the blood sample into the monolith; sequester the blood cells from the blood sample in a first zone; wick the BCF fraction of the blood sample through the first zone and optionally into a second zone of the monolith; and have a measured red blood cell retention factor (Rf) value in the range of 0.01 to 0.8.

A fractionating monolith can include inorganic beads coated with an organic porous polymer coating, wherein the inorganic beads are comprised of silica, metals, and/or metal oxides. The polymer coating can be the same or similar to the polymer in the rest of the monolith.

The wicking test measures the distance water will travel vertically through a monolith cured with dimensions: 1.27 cm wide, 6.35 cm long, 0.30 cm thickness. The monolith is prepared as described herein.

Prior to testing, the monolith was stored in atmospheric conditions (temperature: 18-22° C., RH 10-40%), although the inventors have found that no environmental control is required for monoliths that have not been loaded with environmentally-sensitive reagents (for example, through immobilization/covalent grafting). The measurement may be made visually, by observing the solvent front.

1. 3 mm of the monolith is submerged in de-ionized water with the monolith in the upright orientation;
2. The water moves vertically up the length of the monolith due to wicking action;
3. The distance traveled by the water over the course of 2.0 minutes is measured at the corner of the monolith having the greatest measurement.

A dye may be added to aid measurement. Suitably the dye is a dye that travels with the water without being significantly retarded by the monolith. Suitable examples include FD&C Yellow number 1 and fluorescein. Red 40 and Blue 1 may be also be used for some monoliths as described herein.

The blood-cell-free (herein BCF) zone does not contain any visible red blood cells (erythrocytes) or native white blood cells (leukocytes), but may contain prokaryotic cells, unicellular eukaryotic cells, fungal cells or cell aggregates, or viral particles. The zone may contain cell derivatives such as platelets, exosomes, membrane fragments, and/or biomolecules such as nucleic acids, proteins, peptides, carbohydrates and lipids.

Figure 15:
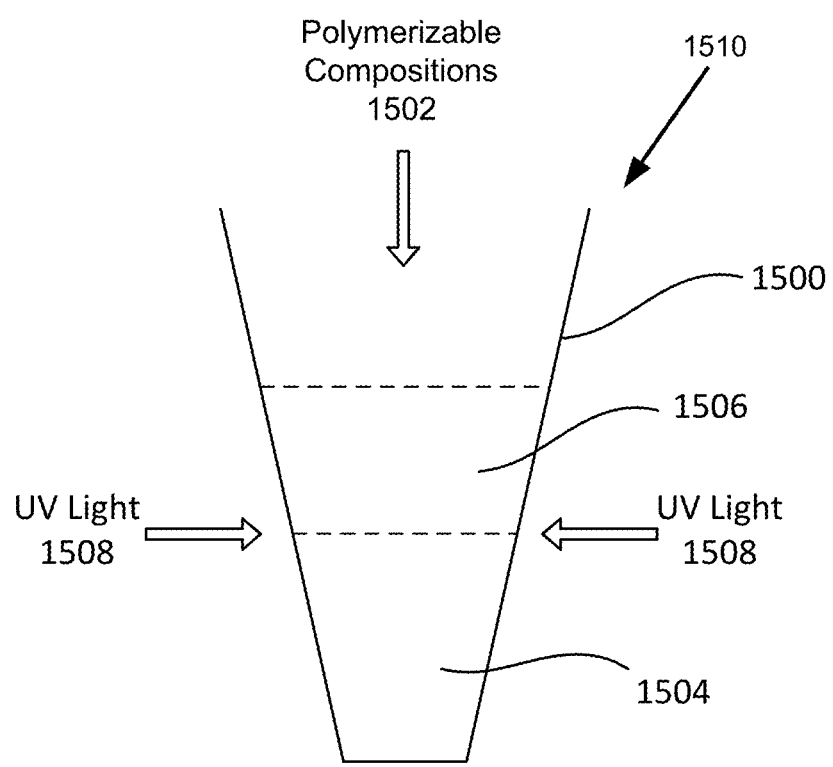
FIG. 15 shows a cross sectional view of a pipette tip configured to make a multilayer porous polymer monolith from a plurality of polymerizable compositions with different volumetric mass densities.

FIG. 15 illustrates a cross sectional view of a pipette tip 1500 configured to make a multilayer porous polymer monolith 1510 from a plurality of polymerizable compositions having different volumetric mass densities. Here, the pipette tip 1500 has a conical cavity with an opening at the top. The narrow end of the pipette tip is sealed liquid-tight. The wall of the pipette tip is transparent to the passage of UV light, if UV light is used to initiate polymerization.

A plurality of polymerizable compositions 1502 may be dispensed sequentially into the conical cavity of pipette tip 1500. A first polymerizable composition comprising a mixture of a plurality of monomers and a porogenic solvent is dispensed into pipette tip 1500 forming a first layer 1504. A second polymerizable composition comprising a mixture of a plurality of monomers and a porogenic solvent is dispensed into pipette tip 1500 forming a second layer 1506. To form layers within monolith 1510, the first composition will have a higher volumetric mass density than the second composition to minimize the mixing of the two compositions.

Initiation of polymerization can be performed using electromagnetic radiation, such as UV light, heating, chemical reaction or combinations thereof. If initiation of polymerization is by UV light, multiple UV light sources 1508 can be positioned around pipette tip 1500 with the UV light directed towards the polymerizable compositions in layers 1504 and 1506 to initiate polymerization of the compositions to form a multilayer monolith 1510 within pipette tip 1500.

Figure 16:
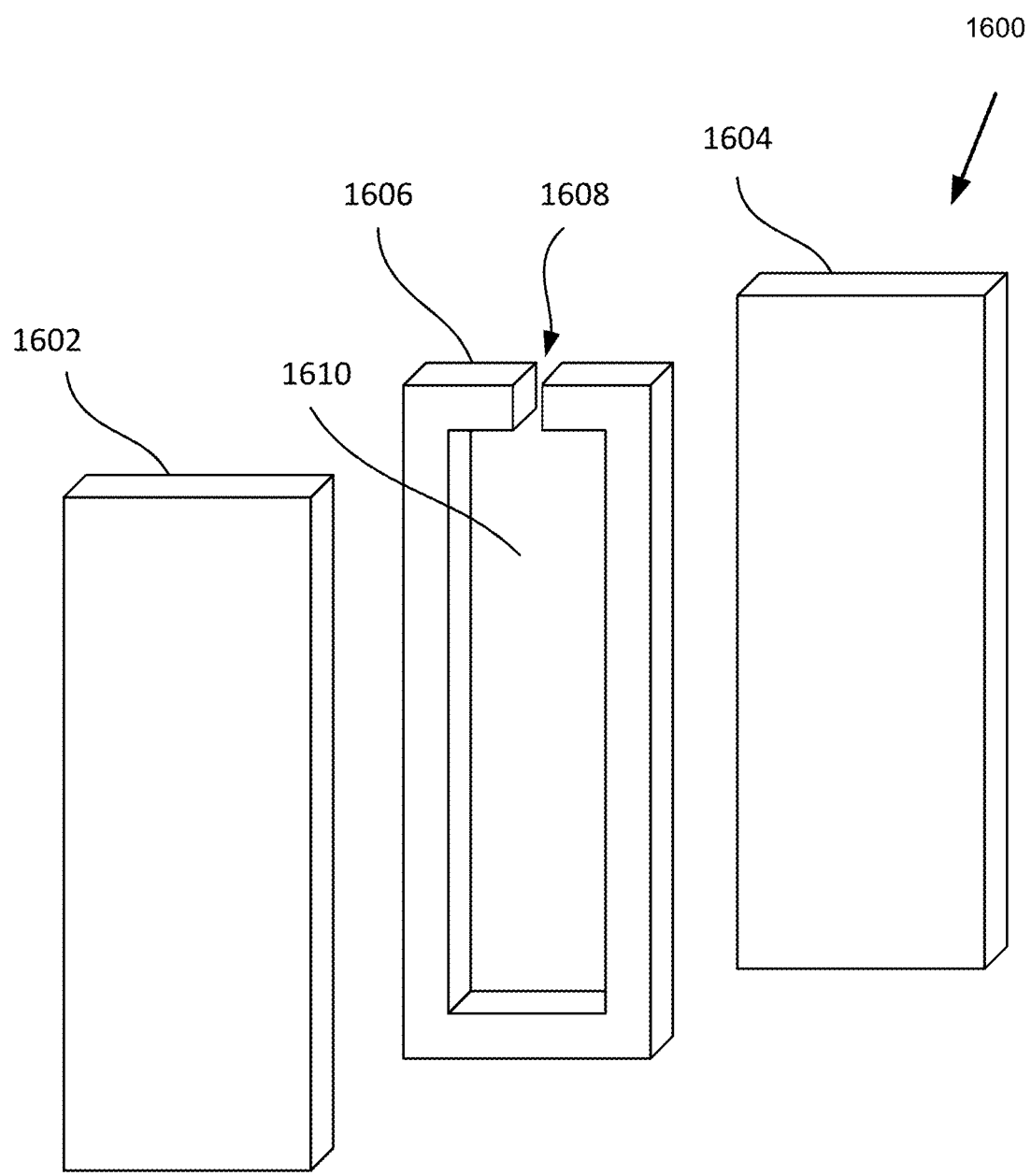
FIG. 16 shows a view of the components of a mold for the fabrication of a multilayer porous polymer monolith with a block or slab shape.

FIG. 16 shows a view of the components of a mold 1600 for the fabrication of a multilayer porous polymer monolith with a block or slab shape. A first flat sheet 1602 and a second flat sheet 1604 enclose an inner mold part 1606 when clamped together to form a mold for making a multilayer monolith. Each sheet 1602 and 1604 has inner and outer flat surfaces. Each sheet 1602 and 1604 is sized to a length and width to enclose the hollow inner cavity 1610 of mold part 1606 when the first sheet 1602 and the second sheet 1604 are clamped on opposite sides of inner mold part 1606. The first sheet 1602 and second sheet 1604 are suitably transparent to the passage of UV light, if UV light is used to initiate polymerization. Initiation of polymerization can be performed using electromagnetic radiation, such as UV light, heating, chemical reaction or combinations thereof.

Mold part 1606 has a hollow inner cavity 1610 with an opening 1608 at the upper end for receiving a sequence of polymerizable compositions when the components of mold 1600 are clamped together. A first polymerizable composition comprising a mixture of a plurality of monomers and a porogenic solvent is dispensed into assembled mold 1600 forming a first layer at the bottom of mold cavity 1610. A second polymerizable composition comprising a mixture of a plurality of monomers and a porogenic solvent is dispensed into assembled mold 1600 forming a second layer positioned on top of the first layer. To form horizontal layers within a monolith in assembled mold 1600, the first composition will have a higher volumetric mass density than the second composition to minimize the mixing of the two compositions.

If UV light is used to initiate polymerization of the polymerizable compositions in cavity 1610 of the assembled mold 1600, at least two UV light sources may be positioned adjacent to the outer surfaces of the first sheet 1602 and second sheet 1604 to provide a source of UV light directed towards the polymerizable compositions in the cavity 1610 of the assembled mold 1600. After polymerization is complete, a multilayer monolith will have been formed in assembled mold 1600. Mold 1600 can be disassembled by unclamping mold 1600, then the first sheet 1602 and the second sheet 1604 can be removed from inner mold part 1606 and a multilayer monolith can be removed from inner mold part 1606.

To facilitate disassembly, sheets 1602 and 1604 can be made of materials with non-stick surfaces, such as various plastics or borosilicate glass that will not stick to a fabricated monolith. In another embodiment, to facilitate the disassembly of mold 1600, the inner surfaces of sheets 1602 and 1604 may be coated or covered with a non-stick layer. The non-stick layer may be a layer of polyethylene, a layer of PVC, polypropylene, or other polyolefin polymer or other plastic. The non-stick layer may also be a spray on coating of PTFE or other suitable mold release coating.

It is to be understood that the examples and modifications described herein are for illustrative purposes only and that various modifications or changes in light thereof will be suggested to persons skilled in the art and are to be included within the spirit of this application and the scope of the appended claims.

The invention claimed is:

1. A method of fabricating a porous polymer monolith, comprising:
   providing a plurality of monomers comprising:
   at least one monomer; and
   at least one radically polymerizable trimethylolpropane (TMP)-based monomer having the formula:

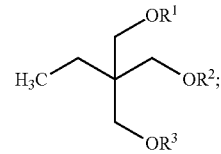

wherein $R^1$, $R^2$, and $R^3$ are each independently selected from —$(CH_2CH_2O)_n$—,
—$(CH_2CH_2O)_nC(O)CH_2CH_2SH$, —$(CH_2CH_2O)_nC(O)CH=CH_2$, and
—$(CH_2CH_2O)_nC(O)C(CH_3)=CH_2$; and each n is independently an integer from 0 to 12:
and wherein the at least one TMP-based monomer comprises trimethylolpropane tris(3-mercaptopropionate) (TMPMP) in an amount ranging from 0.1% to 7% (v:v) of the total volume of the plurality of monomers
obtaining a polymerizable composition by combining the plurality of monomers in a porogenic solvent; and
polymerizing the polymerizable composition to form the porous polymer monolith.

2. The method of claim 1, wherein n is 0.

3. The method of claim 1, wherein the at least one monomer comprises trimethylolpropane ethoxy triacrylate (TMP(EO)TA) in an amount ranging from 0.1% to 44% (v:v) of the total volume of the plurality of monomers.

4. The method of claim 1, wherein the at least one monomer is selected from ethylene glycol dimethacrylate (EGDMA);
   2-hydroxyethyl methacrylate (HEMA);
   tetra(ethylene glycol) diacrylate (TEGDA); and
   tetra(ethylene glycol) dimethacrylate (TEGDMA); or a combination thereof.

5. The method of claim 1, wherein the at least one monomer is selected from
   ethylene glycol dimethacrylate (EGDMA) in an amount ranging from 34% to 75% (v:v) of the total volume of the plurality of monomers;
   2-hydroxyethyl methacrylate (HEMA) in an amount ranging from 10% to 35% (v:v) of the total volume of the plurality of monomers;
   tetra(ethylene glycol) diacrylate (TEGDA) in an amount ranging from 0% to 15% (v:v) of the total volume of the plurality of monomers; and tetra(ethylene glycol) dimethacrylate (TEGDMA) in an amount ranging from 0% to 20% (v:v) of the total volume of the plurality of monomers.

6. The method of claim 1, wherein the porogenic solvent comprises at least one of the following
   alcohols;
   a mixture of alcohols and water;
   a first alcohol of the formula: $[C_XH_{(2X+2)}O]$, wherein X is an integer from 1 to 10; and
   a second alcohol of the formula: $[C_YH_{(2Y+2)}O_2]$, wherein Y is an integer from 2 to 10.

7. The method of claim 1, wherein the porogenic solvent further comprises at least one of the following:
   a surfactant;
   sodium dodecyl sulfate (SDS),
   polyethylene-polypropylene glycol, and
   polyethylene glycol tert-octylphenyl ether.

8. The method of claim 1, wherein the polymerizable composition has a monomer to solvent ratio of 1:1 to 1:5 (v:v).

9. The method of claim 1, wherein the monolith is a self-wicking monolith having a two minute water wick rate between 1.5 and 5.0 centimeters.

10. The method of claim 1, wherein the monolith has a measured red blood cell retention factor (Rf) value in the range of 0.01 to 0.8.

11. The method of claim 1, wherein the monolith has a pore size within a range of 2-7 microns and a porosity of 50 to 85 percent.

12. The method of claim 1, wherein the monolith is a lateral flow monolith.

13. The method of claim 1, wherein the monolith is a lateral flow porous monolith for the fractionation of a blood sample into blood cells and a blood-cell-free fraction.

14. The method of claim 1, wherein the monolith has a minimum tensile strength corresponding to a supported weight of at least 10 grams.

15. A monolith fabricated by the method of claim 1.

* * * * *